(12) United States Patent
Wang et al.

(10) Patent No.: US 11,517,668 B2
(45) Date of Patent: Dec. 6, 2022

(54) EXPANDABLE DRIP CHAMBER

(71) Applicant: CareFusion 303, Inc., San Diego, CA (US)

(72) Inventors: Vincent Wang, San Gabriel, CA (US); Tomas Frausto, Walnut, CA (US); Todd Oda, Torrance, CA (US); Wantjinarjo Suwito, West Linn, OR (US); George Mansour, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 132 days.

(21) Appl. No.: 16/840,024

(22) Filed: Apr. 3, 2020

(65) Prior Publication Data
US 2021/0308372 A1 Oct. 7, 2021

(51) Int. Cl.
*A61M 5/162* (2006.01)
*A61M 5/14* (2006.01)

(52) U.S. Cl.
CPC .......... *A61M 5/162* (2013.01); *A61M 5/1411* (2013.01); *A61M 2005/1402* (2013.01)

(58) Field of Classification Search
CPC ........ A61M 5/1411; A61M 2005/1402; A61M 2005/1403; A61M 5/162; A61M 5/168; A61M 5/1689; A61M 5/1412; A61M 5/00
See application file for complete search history.

(56) References Cited

U.S. PATENT DOCUMENTS

| | | | | |
|---|---|---|---|---|
| 3,965,897 A * | 6/1976 | Lundquist | ........... | A61M 5/1408 604/246 |
| 4,055,176 A * | 10/1977 | Lundquist | ............... | A61M 5/40 604/127 |
| 4,079,736 A * | 3/1978 | Lundquist | ........... | A61M 5/1684 222/49 |
| 4,583,979 A * | 4/1986 | Palti | ..................... | A61M 5/1411 604/251 |
| 5,360,412 A * | 11/1994 | Nakao | .................. | A61M 5/1411 137/395 |
| 2006/0189937 A1* | 8/2006 | Miner | ..................... | A61M 5/36 604/122 |

(Continued)

FOREIGN PATENT DOCUMENTS

WO WO-2011066443 A1 6/2011
WO WO-2017191622 A2 11/2017

OTHER PUBLICATIONS

International Search Report and Written Opinion for Application No. PCT/US2021/025451, dated Jul. 8, 2021, 15 pages.

*Primary Examiner* — Theodore J Stigell
(74) *Attorney, Agent, or Firm* — Morgan, Lewis & Bockius, LLP

(57) ABSTRACT

Drip chambers are described herein. A drip chamber comprises an inlet, an outlet, and a chamber body. The chamber body defines a chamber volume in fluid communication with the inlet and the outlet. The chamber body is movable between a collapsed configuration having a first volume and an expanded configuration having a second volume. The second volume is larger than the first volume, and the chamber body is configured to be moved from the collapsed configuration to the expanded configuration to draw in a medical fluid from the inlet into the chamber volume to prime the drip chamber.

8 Claims, 11 Drawing Sheets

(56) References Cited

U.S. PATENT DOCUMENTS

| | | | | |
|---|---|---|---|---|
| 2008/0097315 A1* | 4/2008 | Miner | ............... | A61M 5/1411 604/122 |
| 2011/0275988 A1* | 11/2011 | Davis | ............... | A61M 5/1411 604/82 |
| 2018/0304009 A1* | 10/2018 | Baid | ............... | A61M 5/16822 |

* cited by examiner

EXPANDABLE DRIP CHAMBER

FIELD OF THE INVENTION

The present disclosure generally relates to drip chambers, and, in particular, to expandable drip chambers.

BACKGROUND

Medical treatments often include the infusion of a medical fluid (e.g., a saline solution or a liquid medication) to patients using an intravenous (IV) catheter that is connected through an arrangement of flexible tubing and fittings, commonly referred to as an "IV set," to a source of fluid, for example, an IV bag. Prior to operation, components of the IV set can be primed with medical fluid.

SUMMARY

In some applications, drip chambers may require repetitive manual action to be primed with medical fluid.

The disclosed subject matter relates to drip chambers. In certain embodiments, a drip chamber comprises an inlet, an outlet, and a chamber body. The chamber body defines a chamber volume in fluid communication with the inlet and the outlet. The chamber body is movable between a collapsed configuration having a first volume and an expanded configuration having a second volume. The second volume is larger than the first volume, and the chamber body is configured to be moved from the collapsed configuration to the expanded configuration to draw in a medical fluid from the inlet into the chamber volume to prime the drip chamber.

In certain embodiments, a method to prime a drip chamber is disclosed and comprises expanding a chamber body from a first volume to a second volume; and drawing in a medical fluid into the chamber body during the expanding the chamber body.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

The disclosed drip chamber incorporates an expandable chamber to allow the drip chamber to be primed in a single action. By priming the drip chamber in a single action, repetitive manual actions can be avoided.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding. Reference numbers may have letter suffixes appended to indicate separate instances of a common element while being referred to generically by the same number without a suffix letter.

While the following description is directed to priming of medical fluid by expanding a disclosed drip chamber, it is to be understood that this description is only an example of usage and does not limit the scope of the claims. Various aspects of the disclosed drip chambers may be used in any application where it is desirable to prime the flow of fluid.

The disclosed drip chamber overcomes several challenges discovered with respect to certain conventional drip chambers. One challenge with certain conventional drip chambers is that certain conventional drip chambers may require repetitive manual actions to draw in sufficient medical fluid to prime the drip chamber. Further, certain conventional drip chambers may occupy excessive storage space. Because repetitive manual actions may cause clinicians to experience fatigue and minimizing storage space is desired, the use of conventional drip chambers is not desirable.

Therefore, in accordance with the present disclosure, it is advantageous to provide a drip chamber as described herein that allows for priming with a single action and storage in a compact configuration. The disclosed drip chamber provides an expandable chamber body that allows for single action priming and compact storage.

An example of a drip chamber that allows for single action priming and compact storage is now described.

Figure 1:
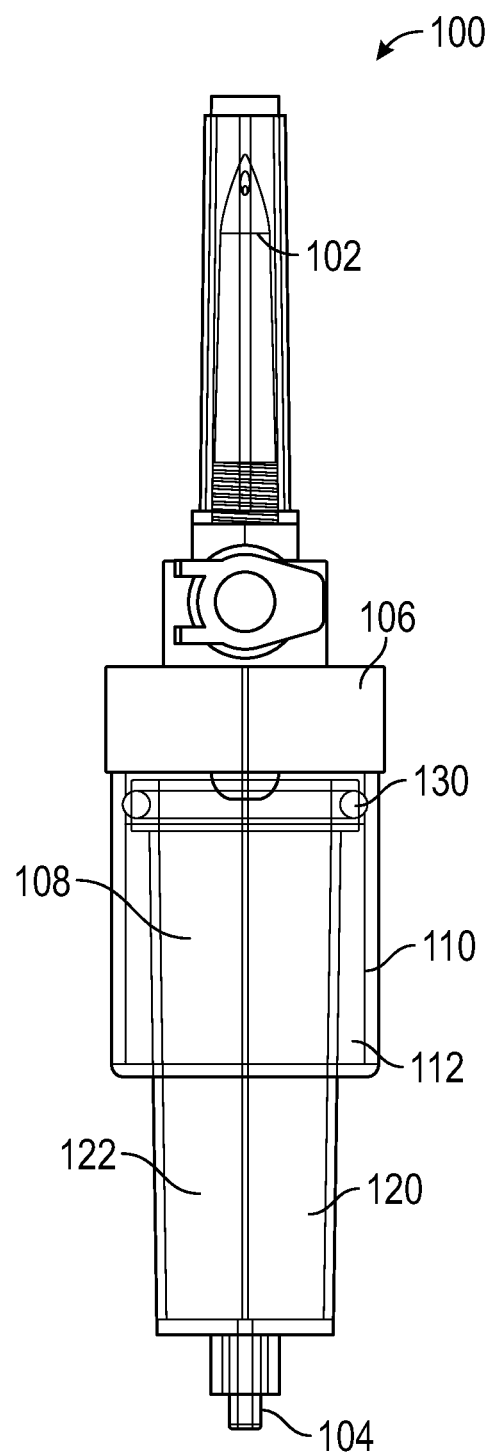
FIG. 1 is a front elevation view of a drip chamber in a collapsed configuration, in accordance with various aspects of the present disclosure.
Figure 2:
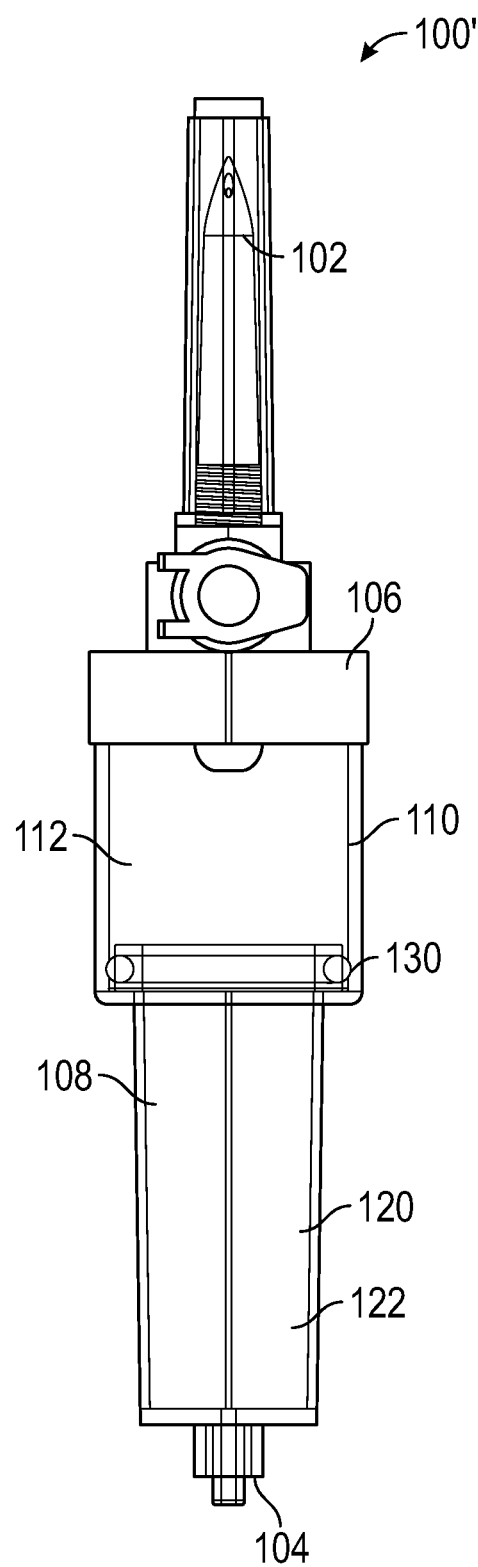
FIG. 2 is a front elevation view of the drip chamber of FIG. 1 in an expanded configuration, in accordance with various aspects of the present disclosure.
Figure 3:
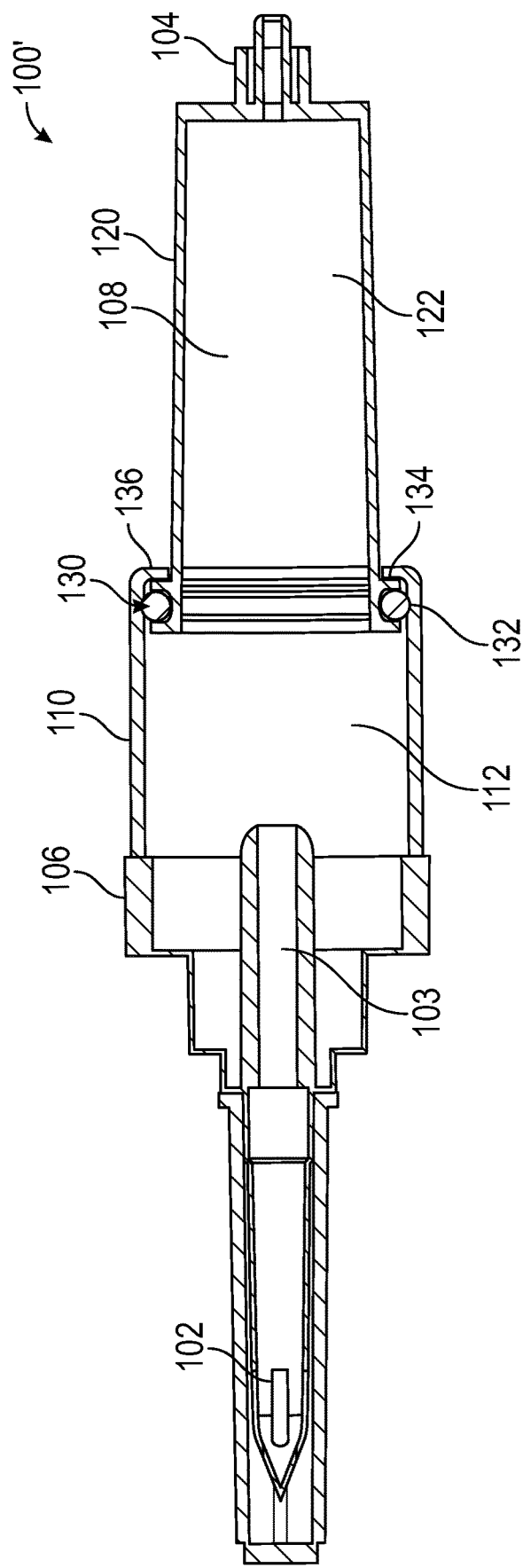
FIG. 3 is a cross-sectional view of the drip chamber of FIG. 1 in an expanded configuration, in accordance with various aspects of the present disclosure.

FIG. 1 is a front elevation view of a drip chamber 100 in a collapsed configuration, in accordance with various aspects of the present disclosure. FIG. 2 is a front elevation view of the drip chamber 100' of FIG. 1 in an expanded configuration, in accordance with various aspects of the present disclosure. FIG. 3 is a cross-sectional view of the drip chamber 100' of FIG. 1 in an expanded configuration, in accordance with various aspects of the present disclosure. With reference to FIGS. 1-3, the drip chamber 100 provides a visual indicator of the flow rate of a medical fluid therethrough. Advantageously, clinicians can monitor and adjust the flow rate of the medical fluid based on the visual indicator provided by the drip chamber 100.

During operation, medical fluid can drip or otherwise flow through the chamber volume defined by the chamber body 108. As illustrated, medical fluid can enter the chamber body 108 through an inlet channel 103 in fluid communication with the chamber body 108. Fluid flow can exit the chamber body 108 through an outlet 104. As fluid passes through the chamber body 108, a clinician can utilize the drip chamber 100 as a visual indicator to observe the dripping or flow of medical fluid therethrough. As can be appreciated the chamber body 108 can be transparent or semi-transparent.

Optionally, the drip chamber 100 can include a spike 102 to pierce membranes, such as an IV container membrane. In some embodiments, the inlet channel 103 can be formed through a spike 102 extending into the chamber body 108. The spike 102 can extend from a spike base 106. The spike base 106 can be threaded or otherwise configured to receive the chamber body 108. In some embodiments, the drip chamber 100 can include an air vent to equalize pressure differentials between the chamber volume and the environment during operation.

In the depicted example, the drip chamber 100 can draw in medical fluid for priming of an IV system. As can be appreciated, the chamber body 108 can be filled with a desired volume of medical fluid during the priming operation. As described herein, the drip chamber 100 can be primed with a desired volume of medical fluid in a single action. Advantageously, a clinician may be able to prime the drip chamber 100 to a desired level by using a single hand.

As described herein, the drip chamber 100 can be expanded from a collapsed or reduced volume (as shown in FIG. 1) to an expanded or increased volume (as shown in FIGS. 2 and 3), creating a vacuum within the drip chamber 100 and effectively drawing in medical fluid to prime the drip chamber 100.

In the depicted example, the chamber body 108 can be formed from an upper chamber body 110 defining an upper chamber volume 112 and a lower chamber body 120 defining a lower chamber volume 122. In some embodiments, the inlet channel 103 can be in fluid communication with the upper chamber volume 112. Optionally, the inlet channel 103 can be considered to be defined by the upper chamber body 110. In some embodiments, the outlet 104 is in fluid communication with the lower chamber volume 122. Optionally, the outlet 104 is defined by the lower chamber body 120.

As described herein, the lower chamber body 120 is movable relative to the upper chamber body 110. In some embodiments, the lower chamber body 120 is axially movable relative to the upper chamber body 110. Further, the upper chamber volume 112 and the lower chamber volume 122 can cooperatively define the overall volume of the drip chamber 100.

With reference to FIG. 1, the drip chamber 100 is shown in an initial or collapsed configuration. In the depicted example, the lower chamber body 120 is at least partially disposed within the upper chamber volume 112. In some applications, the lower chamber body 120 is moved inward to position the lower chamber body 120 adjacent to the inlet channel 103, permitting fluid communication between the inlet channel 103 and the lower chamber volume 122. As illustrated in the collapsed configuration, an upper edge of the lower chamber body 120 can be positioned toward an upper edge of the upper chamber body 110. In some embodiments, the upper edge of the lower chamber body 120 is disposed adjacent to the spike base 106. Advantageously, due to the collapsed configuration of the drip chamber 100, the packaging and storage requirements of the drip chamber 100 can be minimized or reduced in comparison to non-collapsible drip chambers.

In the depicted example, the positioning of the lower chamber body 120 relative to the upper chamber body 110 can define the volume of the drip chamber 100 in the collapsed configuration. In the collapsed configuration, the reduced or initial volume of the drip chamber 100 can be defined by the lower chamber volume 122. As illustrated, in the collapsed configuration, the inlet channel 103 and the outlet 104 of the drip chamber 100 are in fluid communication with the lower chamber volume 122 effectively defining the initial or reduced volume of the drip chamber 100 and bypassing the upper chamber volume 112.

With reference to FIGS. 2 and 3, the drip chamber 100' can be expanded to an increased volume to prime the drip chamber 100'. As illustrated, the lower chamber body 120 can be moved downward or away from the inlet channel 103 to increase or expand the volume of the drip chamber 100'.

In the depicted example, the lower chamber body 120 is generally moved out of the upper chamber volume 112. As described herein, an upper edge portion of the lower chamber body 120 can remain within the upper chamber volume 112. In some applications, the lower chamber body 120 is moved outward to space apart the lower chamber body 120 from the inlet channel 103, permitting fluid communication between the inlet channel 103, the upper chamber volume 112, and the lower chamber volume 122. As illustrated, in the expanded configuration, an upper edge of the lower chamber body 120 can be positioned toward a lower edge of the upper chamber body 110. In some embodiments, the upper edge of the lower chamber body 120 is spaced apart from the spike base 106.

In the depicted example, the positioning of the lower chamber body 120 relative to the upper chamber body 110 can define the volume of the drip chamber 100' in the expanded configuration. In the expanded configuration, the expanded volume of the drip chamber 100 can be defined by a combination of the upper chamber volume 112 and the lower chamber volume 122. As illustrated, in the expanded configuration, the inlet channel 103 and the outlet 104 of the drip chamber 100 are in fluid communication with the upper chamber volume 112 and the lower chamber volume 122 effectively defining the expanded volume of the drip chamber 100'.

In the depicted example, as the drip chamber 100' is expanded to a larger volume, the pressure within the drip chamber 100' decreases due to negative displacement. As can be appreciated, decreased pressure allows the drip chamber 100' to draw in medical fluid, priming the drip chamber 100'. In some embodiments, the difference in volume between the collapsed drip chamber 100 and the expanded drip chamber 100' can be equivalent to the volume of medical fluid that is drawn in during the priming process. As can be appreciated, the difference in volume between the collapsed drip chamber 100 and the expanded drip chamber 100' can be configured to provide a desired amount of medical fluid during the priming process.

Optionally, the chamber body 108 can be formed from a resilient material to allow the chamber body 108 to be squeezed or compressed to draw in medical fluid for additional priming of an IV system.

Figure 4:
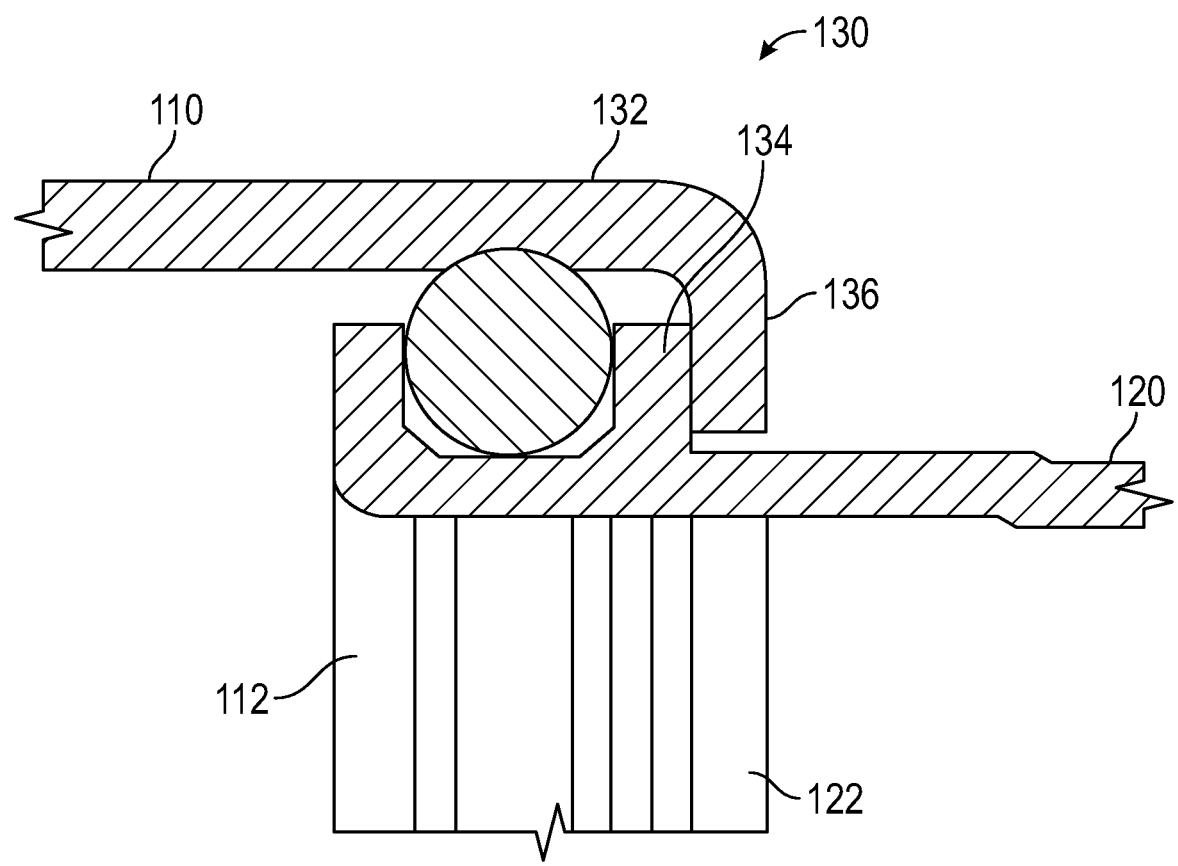
FIG. 4 is a detail view of a seal assembly of the drip chamber of FIG. 3, in accordance with various aspects of the present disclosure.

FIG. 4 is a detail view of a seal assembly 130 of the drip chamber 100 of FIG. 3, in accordance with various aspects of the present disclosure. In some embodiments, the drip chamber 100 can include a seal assembly 130 to prevent leaking between the upper chamber body 110 and the lower chamber body 120. In the collapsed position, the seal assembly 130 can prevent fluid communication between the upper chamber volume 112 and the lower chamber volume 122. In the expanded position, the seal assembly 130 can prevent medical fluid from escaping the chamber body 108 at the interface between the upper chamber body 110 and the lower chamber body 120.

In the depicted example, the seal assembly 130 includes an O-ring 132 disposed between the upper chamber body 110 and the lower chamber body 120. In some embodiments, the O-ring 132 can be retained by a seal groove 134. The seal groove 134 can be formed at an upper edge of the lower chamber body 120. The seal groove 134 can define a race to allow the O-ring 132 to be seated therein.

Optionally, the upper chamber body 110 includes a radial extension 136 to retain the lower chamber body 120 within the upper chamber volume 112. In the depicted example, the radial extension 136 can limit the travel of the lower chamber body 120 to prevent the lower chamber body 120 from being removed from the upper chamber body 110. In some embodiments, the radial extension 136 can extend radially inward to engage with the seal groove 134 of the lower chamber body 120. The engagement of the seal groove 134 and the radial extension 136 can prevent excess travel of the lower chamber body 120.

Figure 5:
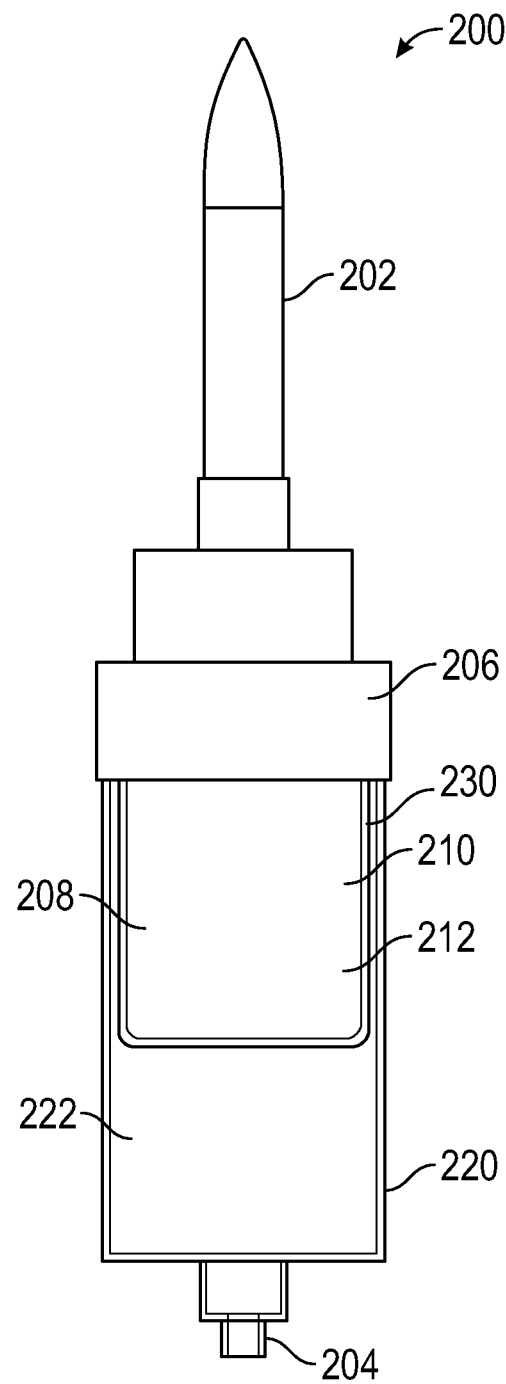
FIG. 5 is a front elevation view of a drip chamber in a collapsed configuration, in accordance with various aspects of the present disclosure.
Figure 6:
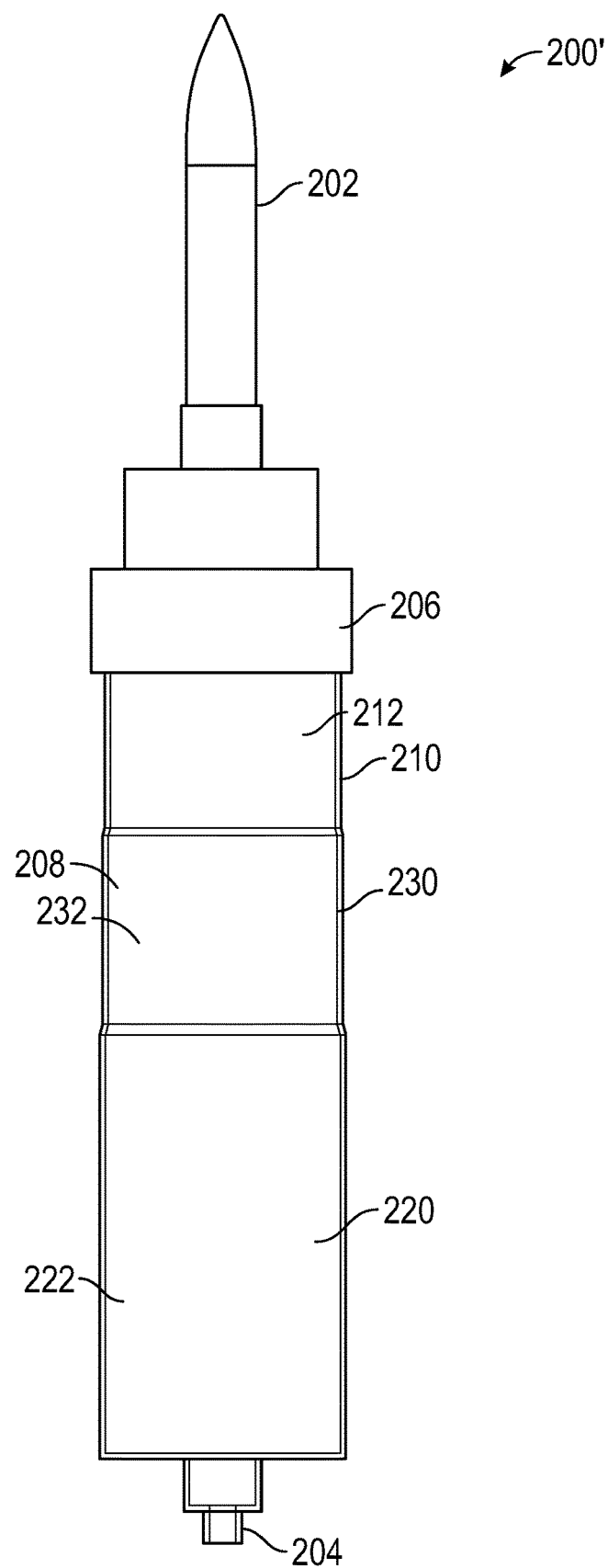
FIG. 6 is a front elevation view of the drip chamber of FIG. 5 in an expanded configuration, in accordance with various aspects of the present disclosure.
Figure 7:
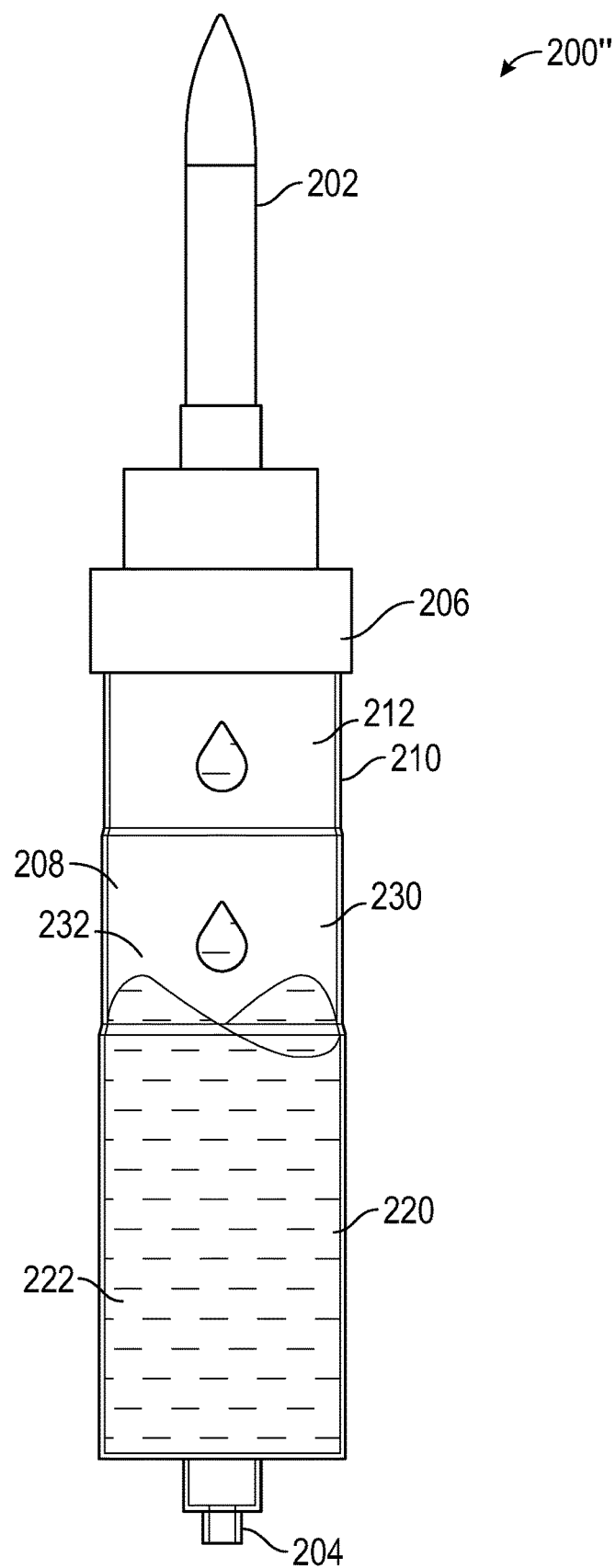
FIG. 7 is a front elevation view of a drip chamber of FIG. 6 in a primed configuration, in accordance with various aspects of the present disclosure.

FIG. 5 is a front elevation view of a drip chamber 200 in a collapsed configuration, in accordance with various aspects of the present disclosure. FIG. 6 is a front elevation view of the drip chamber 200' of FIG. 5 in an expanded configuration, in accordance with various aspects of the present disclosure. FIG. 7 is a front elevation view of the drip chamber 200' of FIG. 6 in an primed configuration, in accordance with various aspects of the present disclosure. With reference to FIGS. 5-7, the drip chamber 200 is a single-piece drip chamber that allows priming with a single action.

As described herein, the drip chamber 200 can be expanded from a collapsed or reduced volume (as shown in FIG. 5) to an expanded or increased volume (as shown in FIG. 6), creating a vacuum within the drip chamber 200 and effectively drawing in medical fluid to prime the drip chamber 200 (as shown in FIG. 7).

In the depicted example, the chamber body 208 can be formed from an upper chamber body 210 defining an upper chamber volume 212, a lower chamber body 220 defining a lower chamber volume 222, and an intermediate chamber body 230 defining an intermediate chamber volume 232. In some embodiments, the intermediate chamber body 230 connects or couples the upper chamber body 210 and the lower chamber body 220. In some embodiments, an inlet, formed through the spike 202 can be in fluid communication with the upper chamber volume 212. Optionally, the inlet can be considered to be defined by the upper chamber body 210. In some embodiments, the outlet 204 is in fluid communication with the lower chamber volume 222. Optionally, the outlet 204 is defined by the lower chamber body 220.

As described herein, the lower chamber body 220 is sliding/movable relative to the upper chamber body 210. In some embodiments, the lower chamber body 220 is axially movable relative to the upper chamber body 210. In some embodiments, the intermediate chamber body 230 can be deformed or inverted to allow the lower chamber body 220 to move relative to the upper chamber body 210. Further, the upper chamber volume 212, the lower chamber volume 222, and the intermediate chamber volume 232 can cooperatively define the overall volume of the drip chamber 200.

With reference to FIG. 5, the drip chamber 200 is shown in an initial or collapsed configuration. In the depicted example, the upper chamber body 210 is at least partially disposed within the lower chamber volume 222. In some applications, the lower chamber body 220 is moved inward to position the lower chamber body 220 adjacent to the inlet, permitting fluid communication between the inlet, the upper chamber volume 212, and a portion of the lower chamber volume 222. As illustrated, in the collapsed configuration, an upper edge of the lower chamber body 220 can be positioned toward an upper edge of the upper chamber body 210. In some embodiments, the upper edge of the lower chamber body 220 is disposed adjacent to the spike base 206. As illustrated, the intermediate chamber body 230 is folded or inverted to allow the lower chamber body 220 to be moved into the collapsed position. Advantageously, due to the collapsed configuration of the drip chamber 200, the packaging and storage requirements of the drip chamber 200 can be minimized.

In the depicted example, the positioning of the lower chamber body 220 relative to the upper chamber body 210 can define the volume of the drip chamber 200 in the collapsed configuration. In the collapsed configuration, the reduced or initial volume of the drip chamber 200 can be defined by the upper chamber volume 212 and a portion of the lower chamber volume 222. As illustrated, in the collapsed configuration, the inlet and the outlet 204 of the drip chamber 200 are in fluid communication with the upper chamber volume 212 and a portion of the lower chamber volume 222 effectively defining the initial or reduced volume of the drip chamber 200. As can be appreciated, in the collapsed configuration, the intermediate chamber body 230 does not define an intermediate chamber volume 232.

With reference to FIGS. 6 and 7, the drip chamber 200' can be expanded to an increased volume to prime the drip chamber 200'. As illustrated, the lower chamber body 120 can be moved downward or away from the inlet channel 103 to increase or expand the volume of the drip chamber 100'.

In the depicted example, the lower chamber body 220 is generally moved away from the upper chamber body 210. As illustrated, as the lower chamber body 220 is moved downward or away from the upper chamber body 210, the intermediate chamber body 230 can be unfolded, reverted, or otherwise revealed, defining an intermediate chamber volume 232. In some applications, the lower chamber body 220 is moved outward to space apart the lower chamber body 220 from the inlet, permitting fluid communication between the inlet, the upper chamber volume 212, the intermediate chamber volume 232 and the lower chamber volume 222. As illustrated, in the expanded configuration, the intermediate chamber body 230 can be disposed between the upper chamber body 210 and the lower chamber body 220. In some embodiments, the upper edge of the lower chamber body 220 is spaced apart from the spike base 206.

In the depicted example, the positioning of the lower chamber body 220 relative to the upper chamber body 210 can define the volume of the drip chamber 200' in the expanded configuration. In the expanded configuration, the expanded volume of the drip chamber 200 can be defined by a combination of the upper chamber volume 212, the intermediate chamber volume 232, and the lower chamber volume 222. As illustrated, in the expanded configuration, the inlet and the outlet 204 of the drip chamber 200 are in fluid communication with the upper chamber volume 212, the intermediate chamber volume 232, and the lower chamber volume 222 effectively defining the expanded volume of the drip chamber 200'.

In the depicted example, as the drip chamber 200' is expanded to a larger volume, the pressure within the drip chamber 200' decreases due to negative displacement. As can be appreciated, decreased pressure allows the drip chamber 200' to draw in medical fluid, priming the drip chamber 200'. In some embodiments, the difference in volume between the collapsed drip chamber 200 and the expanded drip chamber 200' can be equivalent to the volume of medical fluid that is drawn in during the priming process. As can be appreciated, the difference in volume between the collapsed drip chamber 200 and the expanded drip chamber 200' can be configured to provide a desired amount of medical fluid during the priming process.

Figure 8:
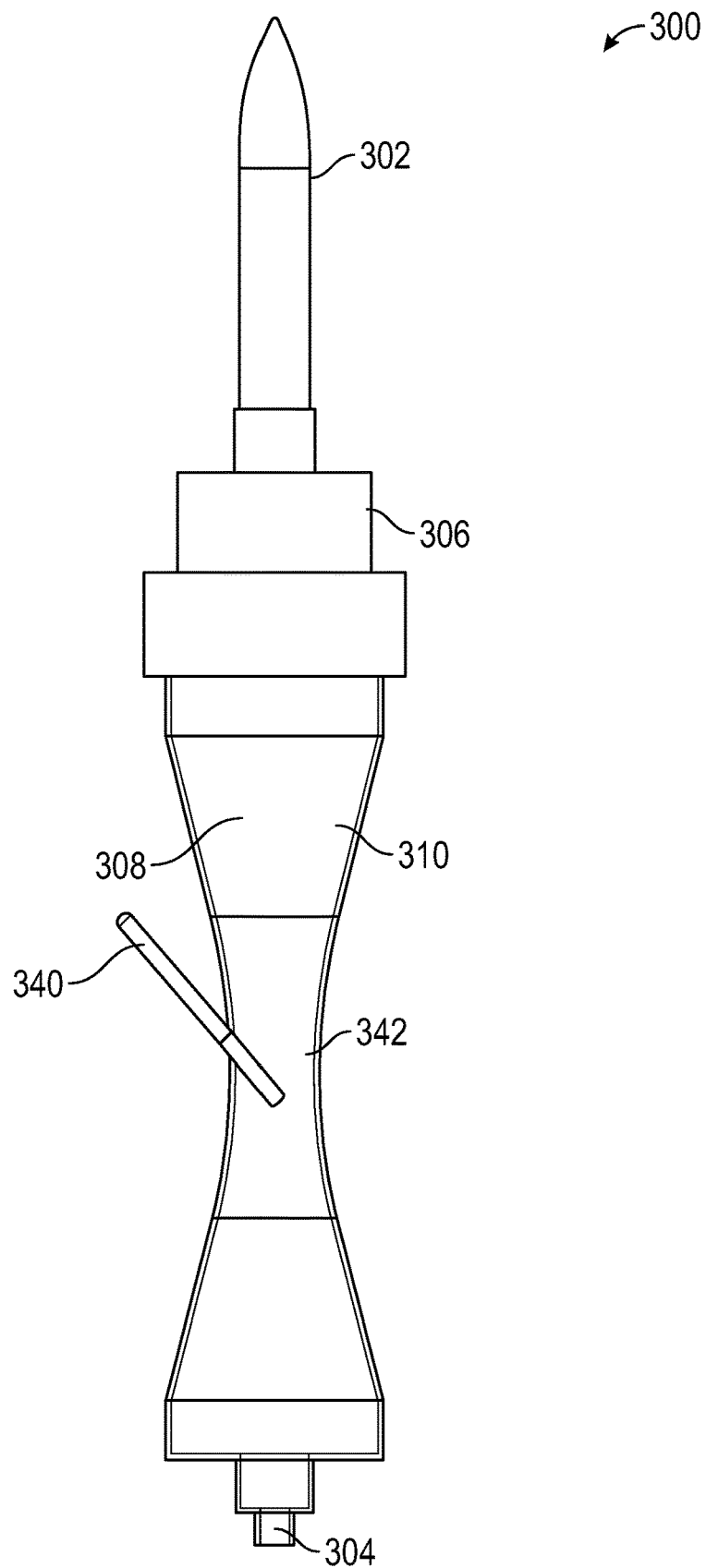
FIG. 8 is a front elevation view of a drip chamber in a collapsed configuration, in accordance with various aspects of the present disclosure.
Figure 9:
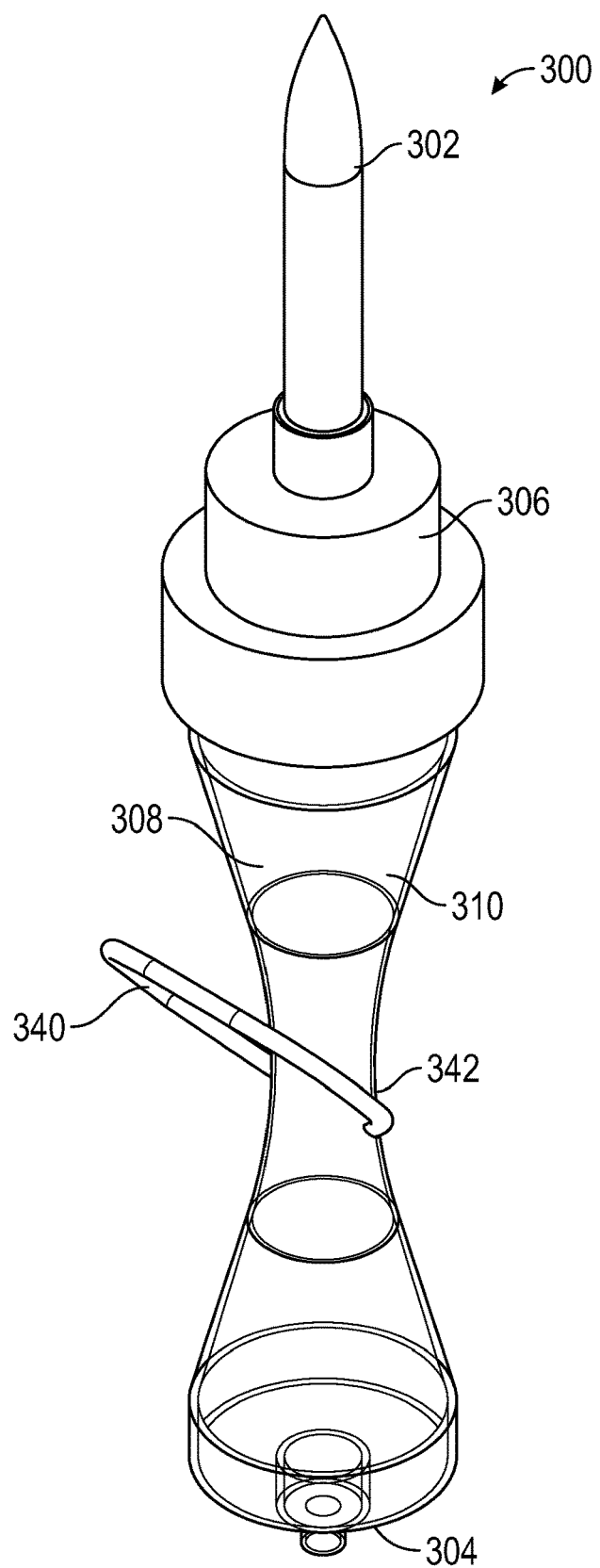
FIG. 9 is a perspective view of a drip chamber of FIG. 8, in accordance with various aspects of the present disclosure.
Figure 10:
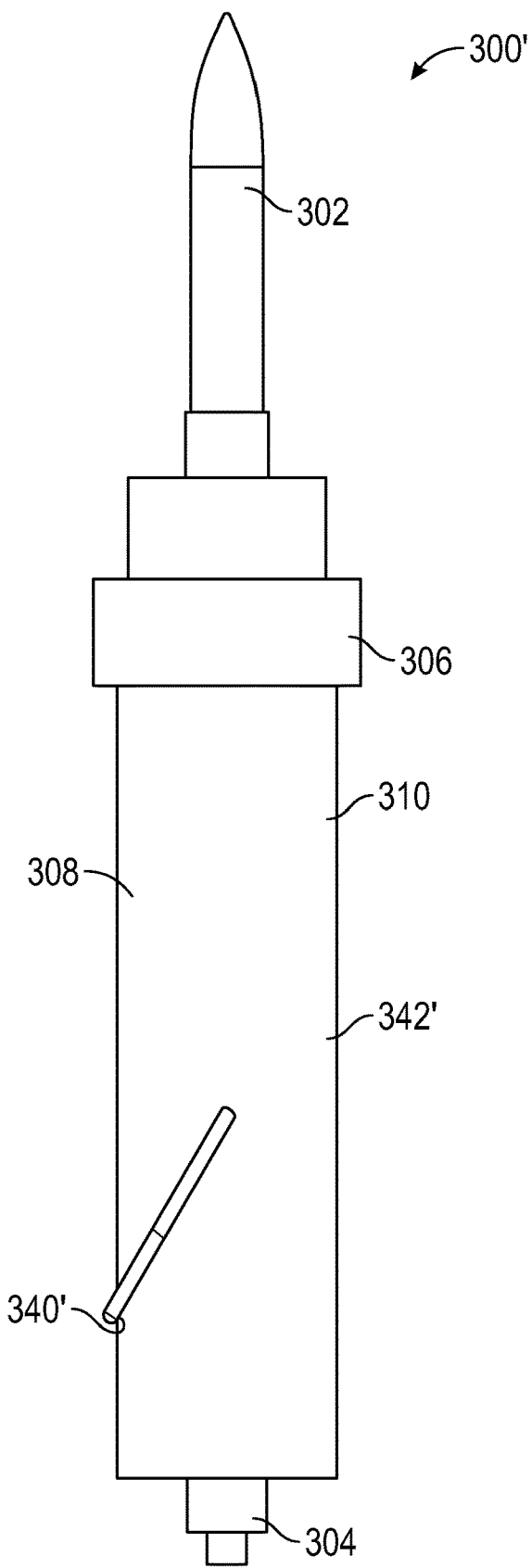
FIG. 10 is a front elevation view of the drip chamber of FIG. 8 in an expanded configuration, in accordance with various aspects of the present disclosure.
Figure 11:
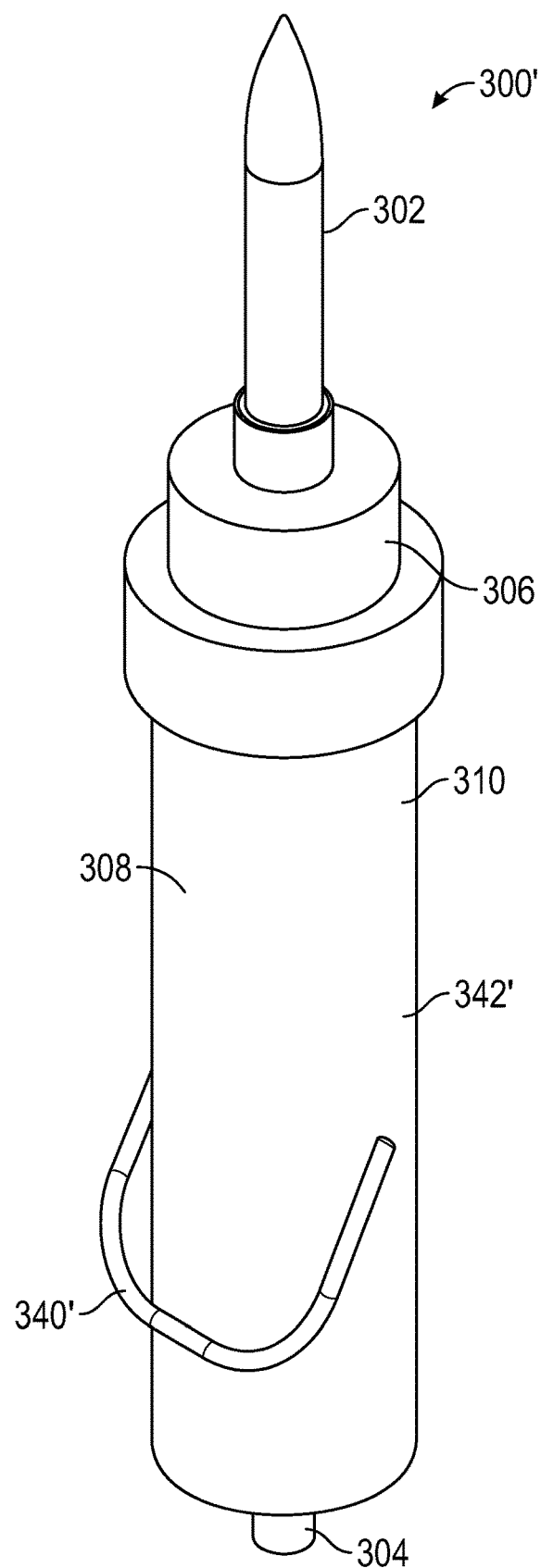
FIG. 11 is a perspective view of the drip chamber of FIG. 10, in accordance with various aspects of the present disclosure.

FIG. 8 is a front elevation view of a drip chamber 300 in a collapsed configuration, in accordance with various aspects of the present disclosure. FIG. 9 is a perspective view of the drip chamber 300 of FIG. 8, in accordance with various aspects of the present disclosure. FIG. 10 is a front elevation view of the drip chamber 300' of FIG. 8 in an expanded configuration, in accordance with various aspects of the present disclosure. FIG. 11 is a perspective view of the drip chamber 300' of FIG. 10, in accordance with various aspects of the present disclosure. With reference to FIGS. 8-11, the drip chamber 300 is a radially expanding drip chamber that allows priming with a single action.

As described herein, the drip chamber 300 can be expanded from a collapsed or reduced volume (as shown in FIGS. 8 and 9) to an expanded or increased volume (as shown in FIGS. 10 and 11), creating a vacuum within the drip chamber 300 and effectively drawing in medical fluid to prime the drip chamber 300.

In the depicted example the chamber body 308 can include a collapsible portion 342. The collapsible portion 342 can radially expand or collapse to adjust the volume of the chamber volume 310. In some embodiments, the collapsible portion 342 is operatively coupled to a lever 340. By moving the lever 340, the collapsible portion 342 can be moved from a reduced radius and volume configuration to an expanded radius and volume configuration. As illustrated, the collapsible portion 342 is in fluid communication with the chamber volume 310, the inlet and the outlet 304.

With reference to FIGS. 8 and 9, the drip chamber 300 is shown in an initial or collapsed configuration. In the depicted example, the collapsible portion 342 has a reduced radius. In some embodiments, the collapsible portion 342 is pressed into a compressed configuration. In some embodiments, the collapsible portion 342 includes overlapping materials that are locked into a compressed configuration. Optionally, the lever 340 can lock in the collapsible portion 342 in the compressed configuration to control the radius of the collapsible portion 342. As can be appreciated, the radius of the collapsible portion 342 can define the volume of the chamber volume 310. In the collapsed configuration, the reduced or initial volume of the drip chamber 300 can be influenced by the radius of the collapsible portion 342. Optionally, the collapsible portion 342 is formed from one or more shape-memory materials.

With reference to FIGS. 8 and 9, the drip chamber 300' can be expanded to an increased volume to prime the drip chamber 300'. In the depicted example, the collapsible portion 342 has an expanded radius. In the expanded configuration, the expanded volume of the drip chamber 300 can be influenced by the radius of the collapsible portion 342. Optionally, the expansion of the drip chamber 300' can be spring loaded or biased. For example, upon triggering the lever 340, the collapsible portion 342 can be biased or urged to expand to a larger radius or volume. In some embodiments, the lever 340 can include a notch or other protrusion that controls the release or unlocking of the collapsible portion 342. By triggering the lever 340, the notch or protrusion can align with a slot or feature in the collapsible portion 342 to permit the collapsible portion 342 to expand form the compressed configuration to the expanded configuration.

In the depicted example, as the drip chamber 300' is expanded to a larger volume, the pressure within the drip chamber 300' decreases due to negative displacement. As can be appreciated, decreased pressure allows the drip chamber 300' to draw in medical fluid, priming the drip chamber 300'. In some embodiments, the difference in volume between the collapsed drip chamber 300 and the expanded drip chamber 300' can be equivalent to the volume of medical fluid that is drawn in during the priming process. As can be appreciated, the difference in volume between the collapsed drip chamber 300 and the expanded drip chamber 300' can be configured to provide a desired amount of medical fluid during the priming process.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A drip chamber comprising:
   an inlet;
   an outlet; and
   a chamber body defining a chamber volume in fluid communication with the inlet and the outlet, wherein the chamber body is movable to maintain a collapsed configuration having a first volume and to maintain an expanded configuration having a second volume, the second volume is larger than the first volume, and the chamber body is configured to be moved from the collapsed configuration to the expanded configuration to draw in a medical fluid from the inlet into the chamber volume to prime the drip chamber, wherein the chamber body comprises:
   an upper chamber body defining an upper chamber volume and the inlet; and
   a lower chamber body defining a lower chamber volume and the outlet,
   wherein the lower chamber body is movable relative to the upper chamber body,
   wherein in the collapsed configuration, the lower chamber body is at least partially disposed within the upper chamber volume and adjacent to the inlet, and the lower chamber volume defines the first volume between the inlet and the outlet, and
   wherein in the expanded configuration, the lower chamber body is spaced apart from the inlet, and the upper chamber volume and the lower chamber volume collectively define the second volume between the inlet and the outlet.

2. The drip chamber of claim 1, further comprising a spike extending from a spike base, wherein the spike base is configured to receive the chamber body.

3. The drip chamber of claim 2, wherein the spike defines the inlet.

4. The drip chamber of claim 1, wherein the lower chamber body is axially movable relative to the upper chamber body.

5. The drip chamber of claim 1, further comprising:
   a seal assembly configured to sealingly engage the upper chamber body and the lower chamber body.

6. The drip chamber of claim 5, wherein the seal assembly comprises:
   an o-ring disposed between the lower chamber body and the upper chamber body.

7. The drip chamber of claim 6, wherein the lower chamber body defines a seal groove to retain the o-ring.

8. The drip chamber of claim 7, wherein the upper chamber body defines a radial extension spaced apart from the inlet, the radial extension configured to engage with the seal groove in the expanded configuration to limit travel of the lower chamber body relative to the upper chamber body.

* * * * *